United States Patent
Kennedy et al.

(10) Patent No.: US 8,367,021 B2
(45) Date of Patent: Feb. 5, 2013

(54) FLUIDIC DEVICES HAVING INCORPORATED ELECTRODES

(75) Inventors: Colin B. Kennedy, Greenbrae, CA (US); Josh Molho, Oakland, CA (US); Alexander V. Dukhovny, San Francisco, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 82 days.

(21) Appl. No.: 13/030,379

(22) Filed: Feb. 18, 2011

(65) Prior Publication Data

US 2011/0139274 A1  Jun. 16, 2011

Related U.S. Application Data

(63) Continuation-in-part of application No. 12/843,557, filed on Jul. 26, 2010, now Pat. No. 8,202,486.

(60) Provisional application No. 61/233,392, filed on Aug. 12, 2009, provisional application No. 61/266,030, filed on Dec. 2, 2009, provisional application No. 61/307,198, filed on Feb. 23, 2010, provisional application No. 61/408,772, filed on Nov. 1, 2010.

(51) Int. Cl.
*F15D 1/00* (2006.01)
*B23P 11/00* (2006.01)

(52) U.S. Cl. .......... 422/502; 422/501; 422/500; 422/50
(58) Field of Classification Search ................. 422/502, 422/501, 500, 50
See application file for complete search history.

(56) References Cited

U.S. PATENT DOCUMENTS

| | | | |
|---|---|---|---|
| 7,033,474 | B1 | 4/2006 | Dubrow et al. |
| 7,517,442 | B1 | 4/2009 | Champagne |
| 2004/0144648 | A1 | 7/2004 | Jacobson et al. |
| 2004/0163958 | A1 | 8/2004 | Kao et al. |
| 2004/0203055 | A1 | 10/2004 | Kennedy et al. |
| 2005/0189224 | A1 | 9/2005 | Parce |
| 2009/0054264 | A1 | 2/2009 | Ugolin et al. |

*Primary Examiner* — Christine T Mui
(74) *Attorney, Agent, or Firm* — Cardinal Law Group

(57) ABSTRACT

The invention provides fluidic devices having incorporated electrodes. One device comprises a card and a caddy. The card includes a channel disposed within the card, first and second vias in fluid communication with the channel through an upper surface of the card, and first and second electrodes disposed on the upper surface of the card. The first via and first electrode are positioned adjacent to a first end of the channel, and the second via and second electrode are positioned adjacent to a second end of the channel. The caddy comprises first and second reservoirs. The caddy is attached to the card such that the first reservoir is positioned over the first via and a portion of the first electrode, and the second reservoir is positioned over the second via and a portion of the second electrode. A portion of each of the electrodes is accessible for dry electrical contact.

36 Claims, 11 Drawing Sheets

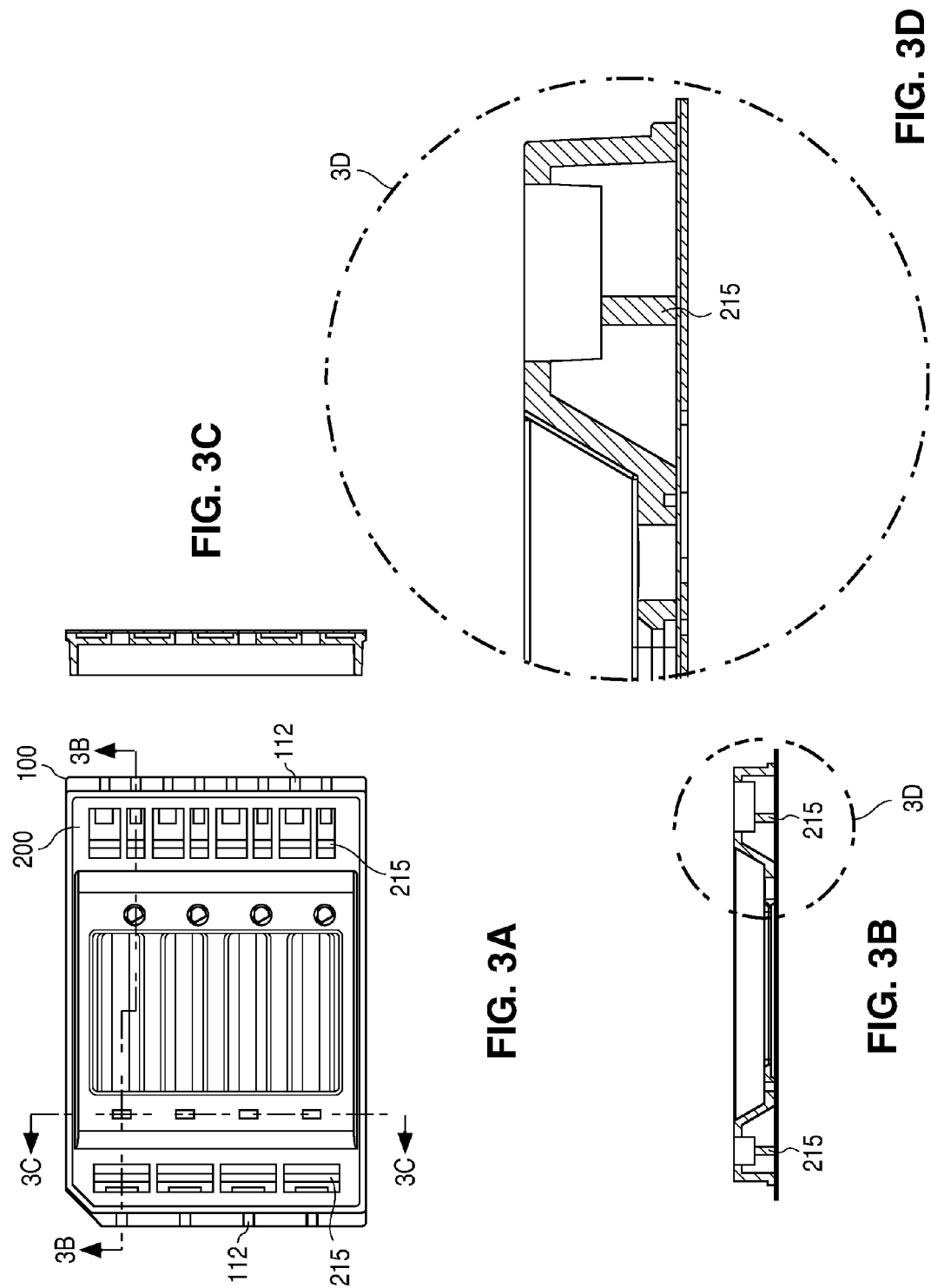

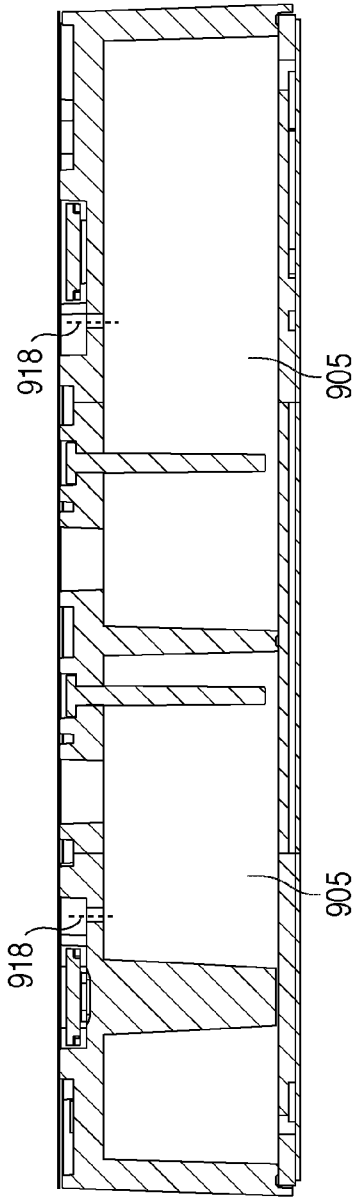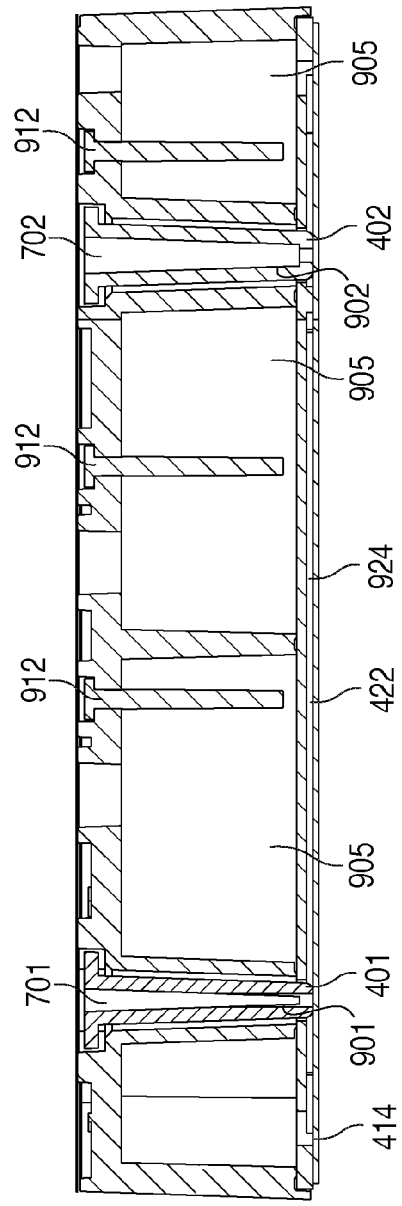

US 8,367,021 B2

FLUIDIC DEVICES HAVING INCORPORATED ELECTRODES

CROSS-REFERENCE TO RELATED APPLICATIONS

This application is a continuation-in-part of, and claims the benefit of, U.S. patent application Ser. No. 12/843,557 filed Jul. 26, 2010, and issued on Dec. 19, 2012, as U.S. Pat. No. 8,202,486, which claims the benefit of and priority to U.S. Provisional Application No. 61/233,392 filed Aug. 12, 2009, and U.S. Provisional Application No. 61/266,030 filed Dec. 2, 2009, the disclosures of which are herein incorporated by reference. This application also claims the benefit of and priority to U.S. Provisional Application No. 61/307,198 filed Feb. 23, 2010, and U.S. Provisional Application No. 61/408,772 filed Nov. 1, 2010, the disclosures of which are herein incorporated by reference.

TECHNICAL FIELD

The present disclosure is in the field of devices, systems, and methods for processing, separating, isolating, and/or analyzing sample components. In particular, described herein are fluidic devices having incorporated electrodes, systems for using such devices, and methods for manufacturing such devices. The invention also provides fluidic devices configured to absorb joule heating within the device.

BACKGROUND OF THE INVENTION

Separations-based analyses are a prominent part of biological research, allowing one to characterize different biological samples, reaction products and the like. Examples of some of the more prevalent separations-based analyses include electrophoretic separations of macromolecular species, e.g., proteins and nucleic acids. Electrophoresis, e.g., capillary electrophoresis, has been established as a highly effective method for separating macromolecular species in order that they might be further characterized. Protein and nucleic acid molecules are two major examples of molecular species that are routinely fractionated and characterized using electrophoretic systems.

Both microfluidic and macrofluidic devices have been applied in separations-based analyses. Examples of novel microfluidic devices and methods for use in the separation of molecular and macromolecular species by electrophoretic means are described in U.S. Pat. Nos. 5,958,694, 6,032,710, and 7,419,784, for example, the entire contents of which are incorporated by reference herein. In such devices, the sample containing the molecular or macromolecular species for which separation is desired is placed in one end of a separation channel located in a fluidic substrate, and a voltage gradient is applied along the length of the channel. As the sample components are electrophoretically transported along the length of the channel and, optionally, through a separation (sieving) matrix disposed therein, those components are resolved. The separated components are then detected at a detection point along the length of the channel, typically near the terminus of the separation channel downstream from the point at which the sample was introduced. Following detection, the separated components may be directed to a collection reservoir/well in the device (or to an external device such as a multiwell plate using a capillary pipettor, for example) for subsequent extraction or disposal.

In many situations, it is desirable to extract selected fragments of interest, such as DNA (deoxyribonucleic acid) fragments, following the separation of the fragments into bands in the separation matrix for further processing or analysis, e.g., restriction enzyme modification, T4 ligation, PCR (polymerase chain reaction) amplification, mass spectroscopy, or polynucleotide kinase reactions. The typical process used by laboratory researchers for extracting and isolating selected DNA fragments of interest (and other desired nucleic acid and protein fragments) from a separation matrix (such as an agarose gel) involves staining the separated fragments and then shining UV (ultraviolet) light on the fragments to visualize the separated bands. A razor blade is then used to manually cut the gel above and below each fragment of interest. The DNA must then be extracted and purified from the gel slice. The recovered DNA can then be used for further processing or analysis. This extraction process, however, is time consuming, laborious, and potentially damaging to the DNA (e.g., nicking of the DNA can occur if the DNA is exposed to UV light too long while the fragments of interest are being illuminated for excision).

Thus, in performing separations-based analyses, it would be desirable to be able to also isolate or extract one or more of the separated components in the device itself for further analysis or processing. The recovered or isolated fragments could then be used for a variety of different processes including, for example, the following: amplification using polymerase chain reaction (PCR); ligation reactions for cloning small to medium-sized strands of DNA into bacterial plasmids, bacteriophages, and small animal viruses to allow the production of pure DNA in sufficient quantities to allow its chemical analysis; reactions to dissolve a separated protein or nucleic acid component in a suitable matrix for further analysis by a mass spectrometer using, for example, Matrix-Assisted Laser Desorption Ionization (MALDI); binding reactions to bind a labeling agent to one or more separated protein or nucleic acid components for further analysis; or other similar post-detection processes. In addition, in the case of PCR samples, it is important to be able to separate smaller dimer and primer molecules from the main nucleic acid fragments in the sample and then isolate and collect the main nucleic acid fragments for further analysis or processing, while directing the smaller primer and dimer components to a waste reservoir/well for removal and subsequent disposal.

Typically, the electrodes used in performing electrophoretic separations in a fluidic device are included in an instrument that receives the fluidic device, rather than in the fluidic device itself. Because the instrument electrodes are not disposable and are used serially with multiple devices, contamination of the samples, reaction mixtures, and reaction products may result. In some separations-based applications, limited contamination is not a problem; however, when a component of interest is to be isolated or extracted from a sample, avoiding contamination of a subsequent sample with components of an earlier sample can be crucial. Therefore, it would be advantageous to provide improved fluidic devices that incorporate electrodes into the devices, eliminating the need for multi-use electrodes being included in the instrument that receives the devices.

SUMMARY OF THE INVENTION

One aspect of the present invention is a fluidic device having incorporated electrodes. A first device comprises a card and a caddy. The card comprises a channel having first and second ends, the channel disposed within the card. The card further comprises first and second vias in fluid communication with the channel through an upper surface of the card and first and second electrodes disposed on the upper surface of the card. The vias in the top portion of the card are oriented such that they are in communication with at least one of the channels and/or chambers formed in the interior portion of the device. The first via and first electrode are positioned adjacent to the first end of the channel, and the second via and second electrode are positioned adjacent to the second end of the channel. The caddy comprises first and second reservoirs. The caddy is attached to the card such that the first reservoir is positioned over the first via and a portion of the first electrode, the second reservoir is positioned over the second via and a portion of the second electrode, and a portion of each of the first electrode and the second electrode is accessible for dry electrical contact.

Another fluidic device having incorporated electrodes comprises a card and a caddy. The card comprises a channel having first and second ends, the channel disposed within the card. The card further comprises a first via in fluid communication with the channel through an upper surface of the card, the first via positioned adjacent to the first end of the channel, and a second via in fluid communication with the channel through the upper surface of the card, the second via positioned adjacent to the second end of the channel. The caddy comprises first and second reservoirs and first and second electrodes. The first electrode is positioned such that a first portion of the first electrode extends into the first reservoir and a second portion of the first electrode is accessible for dry electrical contact, and the second electrode is positioned such that a first portion of the second electrode extends into the second reservoir and a second portion of the second electrode is accessible for dry electrical contact. The caddy is attached to the card such that the first reservoir is positioned over the first via and the second reservoir is positioned over the second via. The electrodes may be disposed on deformable tabs or they may be fabricated as structures independent of the caddy and inserted into openings in the caddy.

Another aspect of the present invention is a fluidic device configured to absorb joule heating within the device, the device comprising a card and a caddy. The card comprises a channel having first and second ends, the channel disposed within the card. The card further comprises first and second vias in fluid communication with the channel through an upper surface of the card. The first via is positioned adjacent to the first end of the channel, and the second via is positioned adjacent to the second end of the channel. The caddy comprises first and second reservoirs. The caddy is attached to the card such that the first reservoir is positioned over the first via and the second reservoir is positioned over the second via. The first reservoir extends over an area covering substantially a first longitudinal half of the channel, and the second reservoir extends over an area covering substantially a second longitudinal half of the channel.

Yet another aspect of the present invention is a system for isolating one or more sample components of a sample material following separation of the sample material into a plurality of sample components. The system comprises a device having incorporated electrodes such as has been described herein, a detector in sensory communication with the device, a fluid direction system, and a processor operably coupled to the detector and the fluid direction system.

Still another aspect of the present invention is a method of manufacturing a fluidic device having incorporated electrodes. A first method comprises providing a card, providing a caddy, and attaching the caddy to the card. The card comprises a channel, first and second vias, and first and second electrodes. The channel is disposed within the card and has first and second ends. The first and second vias are in fluid communication with the channel through an upper surface of the card. The first and second electrodes are disposed on the upper surface of the card. The first via and first electrode are positioned adjacent to the first end of the channel, and the second via and second electrode are positioned adjacent to the second end of the channel. The caddy comprise first and second reservoirs. The caddy is attached to the card such that the first reservoir is positioned over the first via and a portion of the first electrode, the second reservoir is positioned over the second via and a portion of the second electrode, and a portion of each of the first electrode and the second electrode is accessible for dry electrical contact.

A second method comprises providing a card, providing a caddy, and attaching the caddy to the card. The card comprises a channel and first and second vias. The channel is disposed within the card and has first and second ends. The first via is in fluid communication with the channel through an upper surface of the card and is positioned adjacent to the first end of the channel. The second via is in fluid communication with the channel through the upper surface of the card and is positioned adjacent to the second end of the channel. The caddy comprises first and second reservoirs and first and second electrodes. The first electrode is positioned such that a first portion of the first electrode extends into the first reservoir and a second portion of the first electrode is accessible for dry electrical contact, and the second electrode is positioned such that a first portion of the second electrode extends into the second reservoir and a second portion of the second electrode is accessible for dry electrical contact. The caddy is attached to the card such that the first reservoir is positioned over the first via and the second reservoir is positioned over the second via.

The aforementioned and other features and advantages of the invention will become further apparent from the following detailed description of the presently preferred embodiments, read in conjunction with the accompanying drawings, which are not to scale. In the drawings, like reference numbers indicate identical or functionally similar elements. The detailed description and drawings are merely illustrative of the invention, rather than limiting, the scope of the invention being defined by the appended claims and equivalents thereof.

BRIEF DESCRIPTIONS OF THE DRAWINGS

FIG. 3A is a top view of the multilayer fluidic card and caddy illustrated in FIGS. 2A and 2B assembled into a fluidic device; FIGS. 3B and 3C show cross-sectional views of the fluidic device of FIG. 3A, and FIG. 3D shows an enlarged view of a portion of FIG. 3B;

Figure 4A:
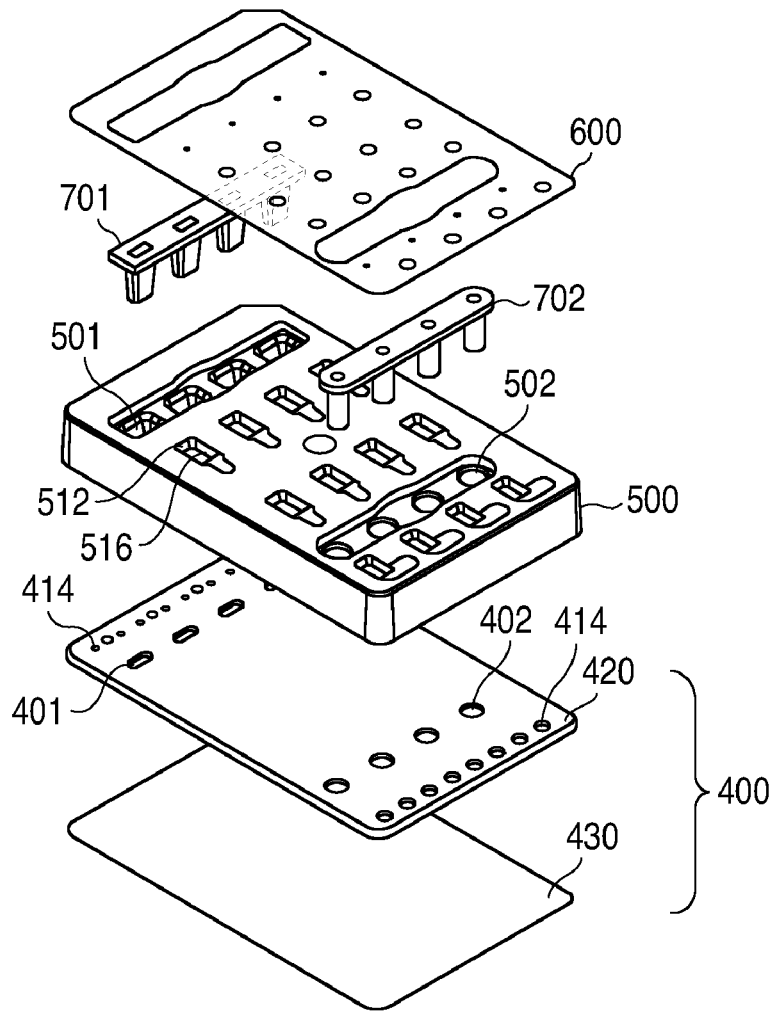
FIGS. 4A and 4B are an exploded view and an assembled view, respectively, of another fluidic device having incorporated electrodes, in accordance with the present invention.
Figure 4B:
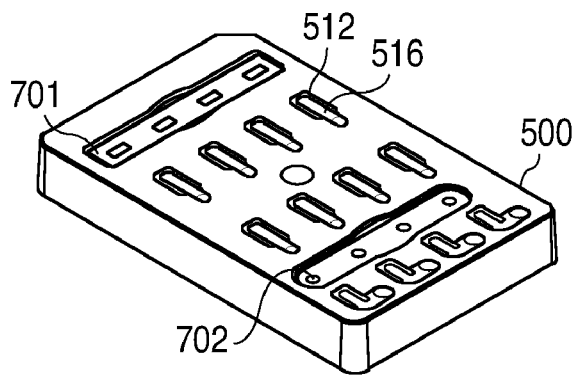
Figure 5A:
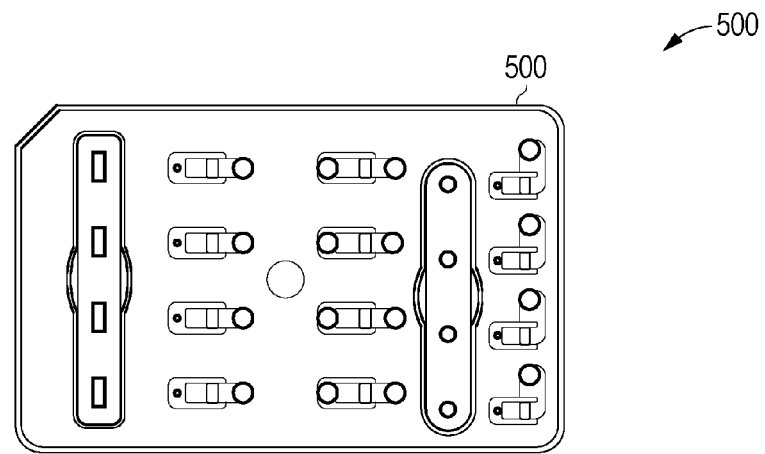
Figure 5B:
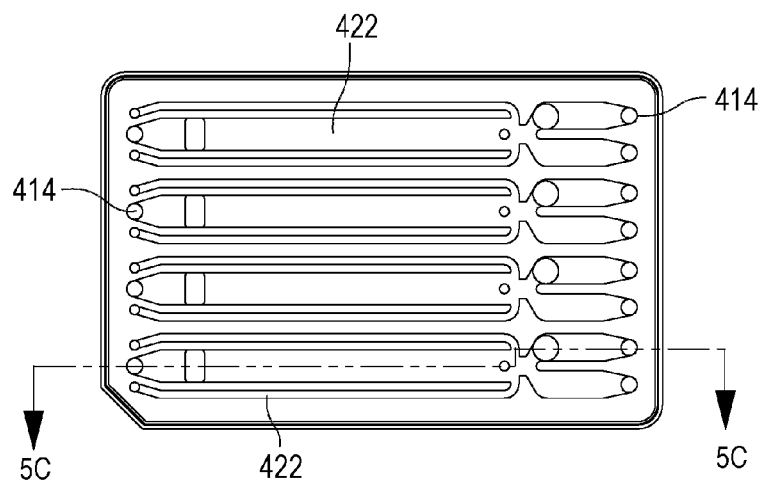
Figure 5C:
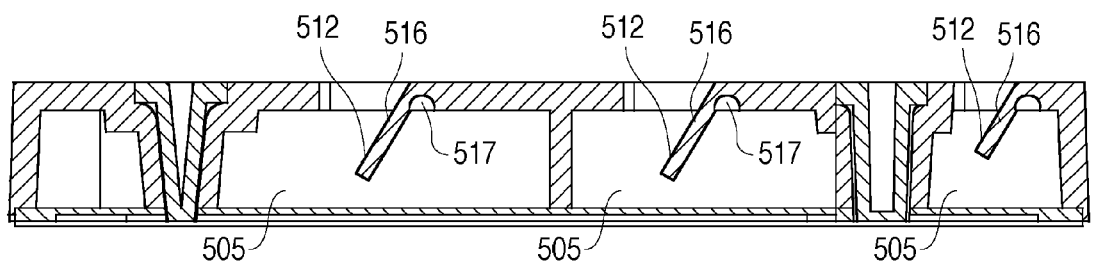
Figure 6A:
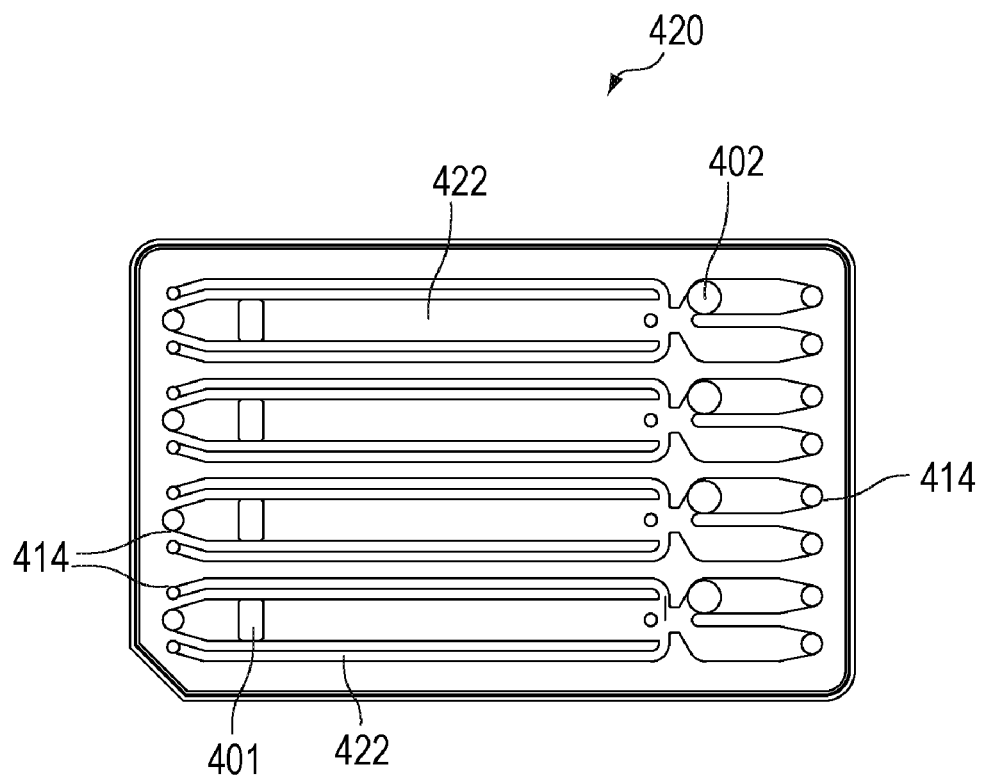
Figure 6B:
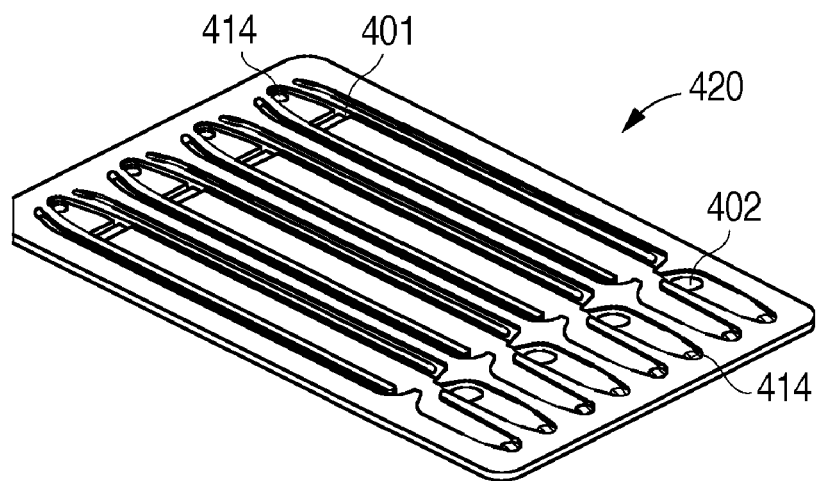
Figure 8A:
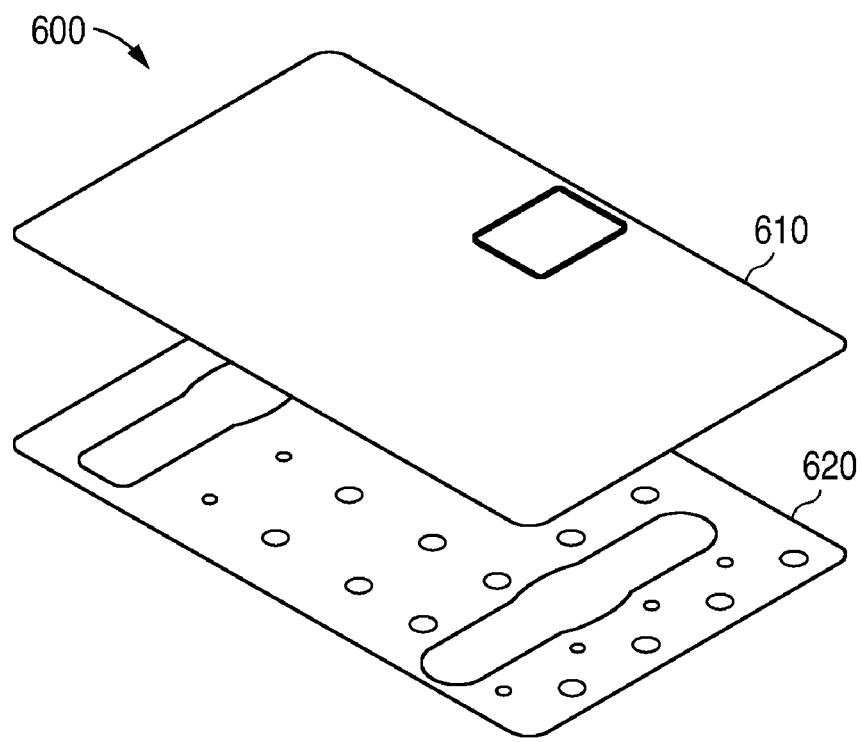
Figure 8B:
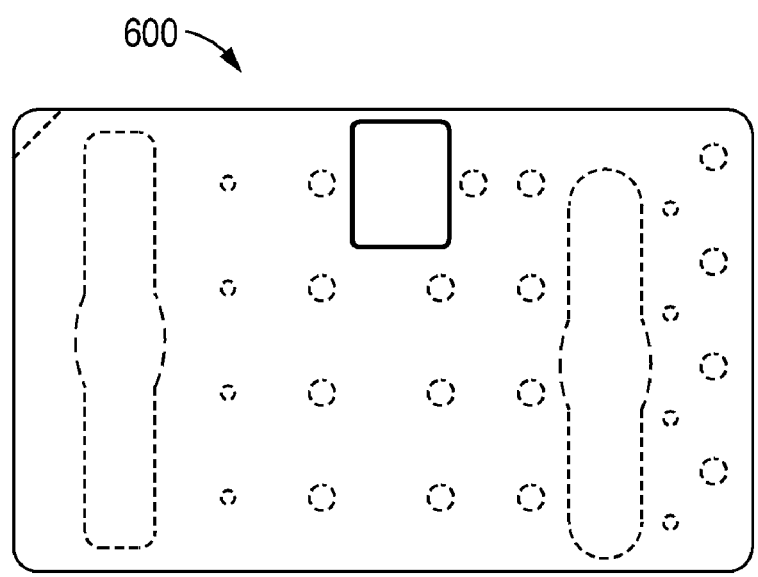
Figure 9A:
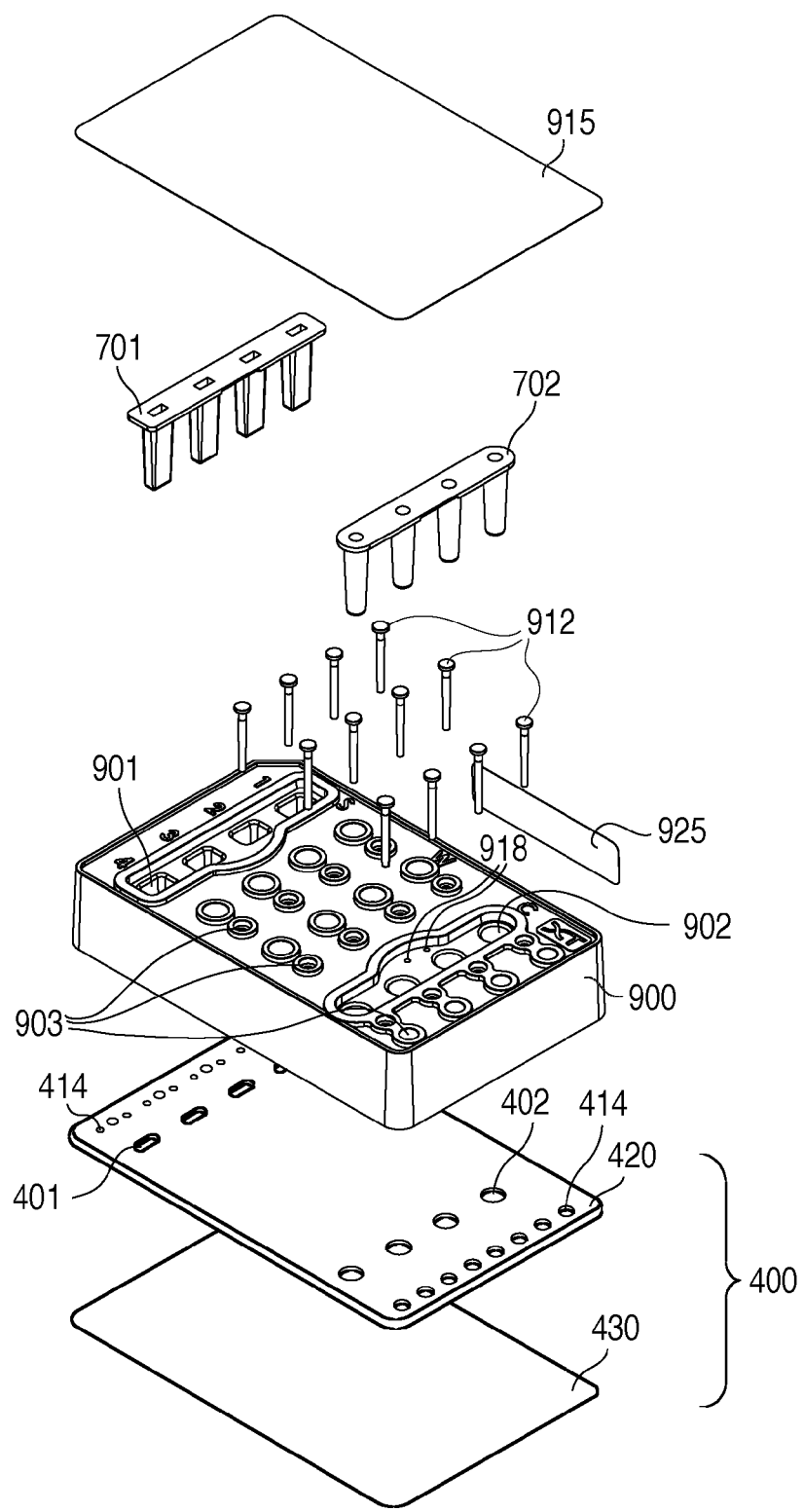
Figure 9B:
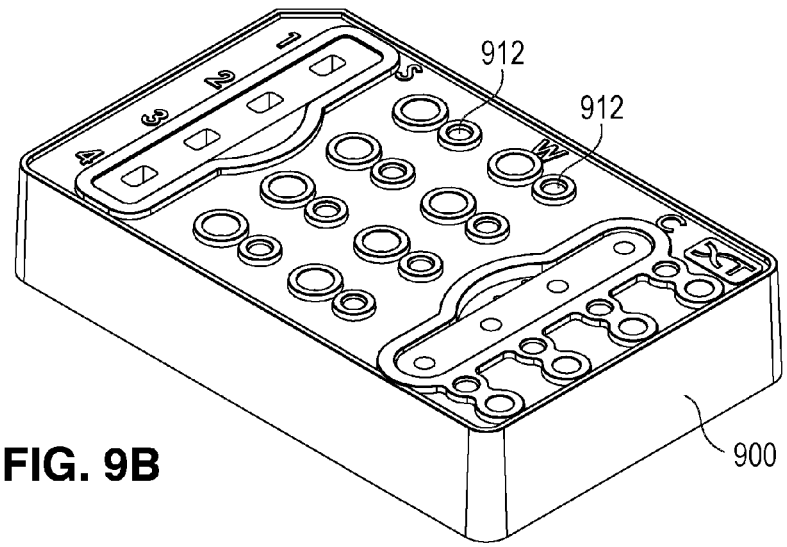
Figure 10A:
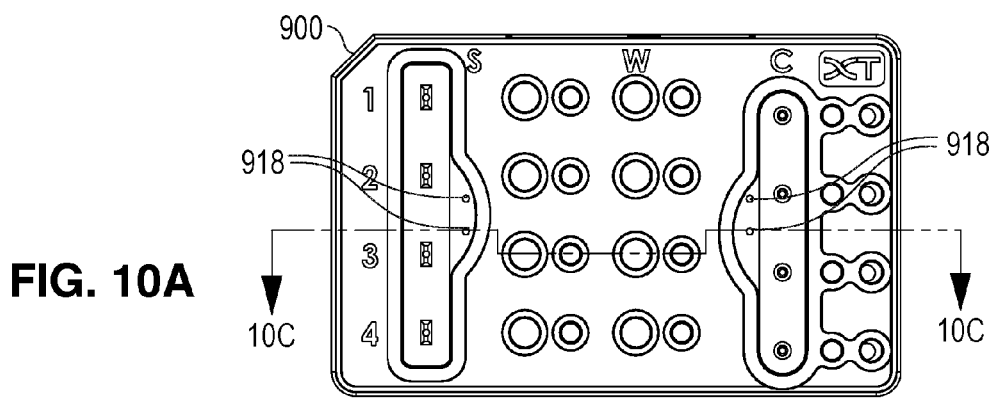
Figure 10B:
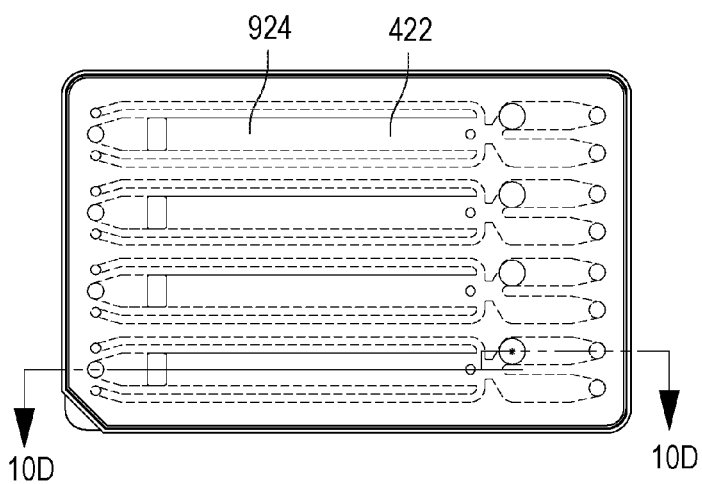

FIGS. 5A, 5B, and 5C are a top view, a bottom view, and a cross-sectional view, respectively, of the fluidic device of FIGS. 4A and 4B, in accordance with the present invention;

FIGS. 6A and 6B are a bottom view and an angled top view, respectively, of a channel sheet, in accordance with the present invention;

FIGS. 7A, 7B, 7C, and 7D are a top view, a bottom view, an angled bottom view, and an angled top view, respectively, of the caddy of FIGS. 4A, 4B, and 5A-5C, in accordance with the present invention, the caddy having incorporated electrodes;

FIGS. 8A and 8B are an exploded view and a top view, respectively, of the patterned/punched label also seen in FIG. 4A, in accordance with the present invention;

FIGS. 9A and 9B are an exploded view and an assembled view, respectively, of yet another fluidic device having incorporated electrodes, in accordance with the present invention; and FIGS. 10A and 10B are a top view and a bottom view, respectively, of the fluidic device of FIGS. 9A and 9B, while FIGS. 10C and 10D are cross-sectional views of the same fluidic device.

DETAILED DESCRIPTION OF THE PRESENTLY PREFERRED EMBODIMENTS

One aspect of the present invention is a fluidic device having incorporated electrodes. The fluidic device comprises a multilayer fluidic card and a caddy. The electrodes of the fluidic device may be incorporated into either the card or the caddy.

One embodiment of a fluidic device having incorporated electrodes, in accordance with the present invention, is illustrated in FIGS. 1A-3D. The device comprises a multilayer fluidic card 100 and a caddy 200. In the present embodiment, the electrodes are incorporated into the multilayer card. Card 100 comprises a top sheet 110, a channel sheet 120, and a bottom sheet 130. Top sheet 110 includes wells 101 and 102, electrodes 112, and vias 114. Channel sheet 120 includes channels 122. Caddy 200 includes wells 201 and 202 and reservoirs 205.

Figure 1A:
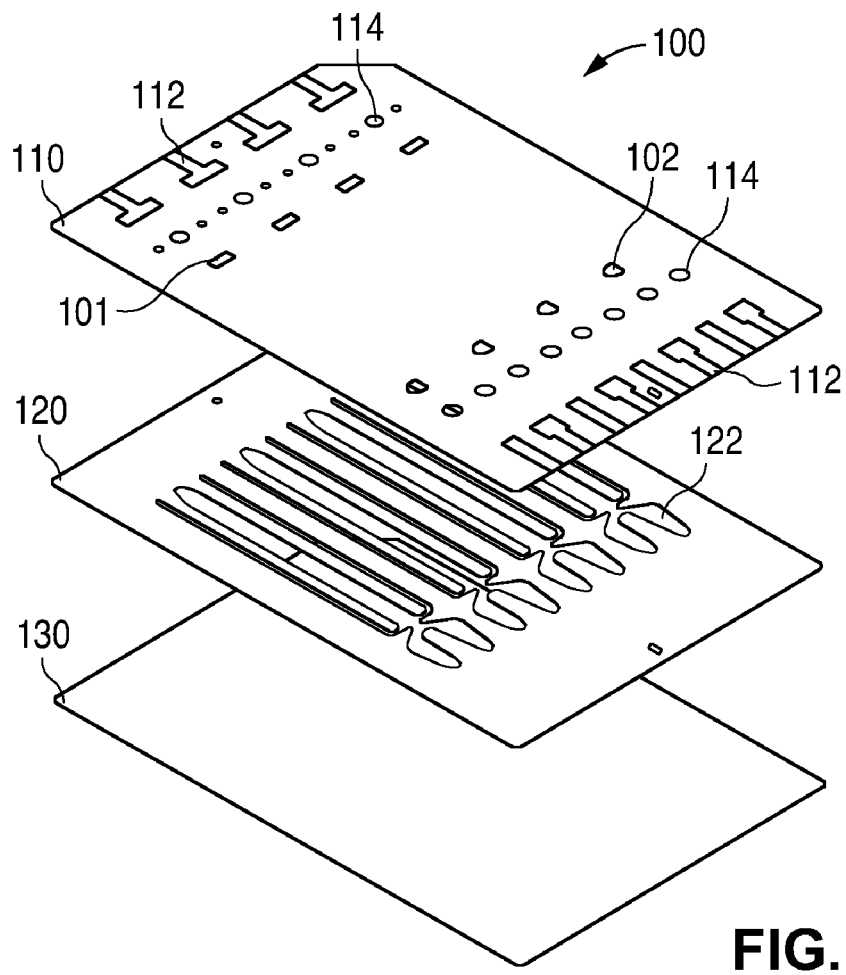
FIGS. 1A and 1B are an exploded view and an assembled view, respectively, of a multilayer fluidic card with incorporated electrodes, in accordance with the present invention.
Figure 1B:
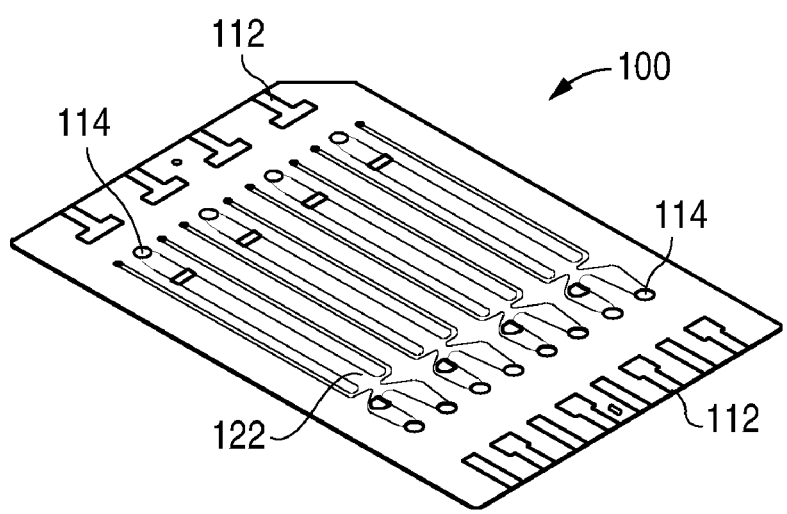

FIG. 1A shows an exploded view of multilayer card 100, while FIG. 1B shows the card assembled. As seen in FIG. 1A, top sheet 110 includes a plurality of electrically isolated electrodes 112 disposed on a top surface of the top sheet and, therefore, disposed on a top surface of the multilayer card. While eight electrodes are shown in FIGS. 1A and 1B positioned on two edges of a substantially rectangular sheet, the number and positioning of the electrodes may vary as may the shape of the card. In the present embodiment, electrodes 112 are fabricated using a carbon conductive paste. In alternative embodiments, the electrodes may comprise different or additional materials, including, for example, gold, copper, platinum, silver/silver chloride paste, and other conductive materials. The electrodes may be patterned onto top sheet 110 by screen printing, pad printing, ink-jet printing, stenciling, or other similar methods. Alternatively, the electrodes may be formed separately and attached to the sheet using methods known in the art.

The electrodes may be fabricated using a single material or multiple materials. For example, multiple materials may be used where one of the electrode materials has high conductivity but is incompatible with liquids to be used in and with the device. In this case, electrodes may be fabricated by applying a chemically compatible material (e.g., a carbon conductive paste) to regions of the device that will come into contact with a liquid, applying a second material (e.g., a high-conductivity material such as silver) outside of the regions of the device that contact a liquid, and connecting the second material to the chemically compatible material. Alternatively, a chemically incompatible conductive material may be applied first to top sheet 110 and then covered completely with a chemically compatible conductive material. In this way, low electrical resistance is achieved, but a liquid within the device is exposed only to a chemically compatible conductive material.

Each via 114 extends through top sheet 110 to provide fluid communication with at least one channel 122 formed in channel sheet 120. Thus, the configuration of vias 114 in top sheet 110 is based on the configuration of the channel or channels 122 in channel sheet 120. While one configuration of vias and channels is illustrated in the figures, other configurations are possible. Vias 114 and channels 122 may be formed using techniques known in the art such as molding, etching, drilling, laser cutting, and punching.

Figure 2A:
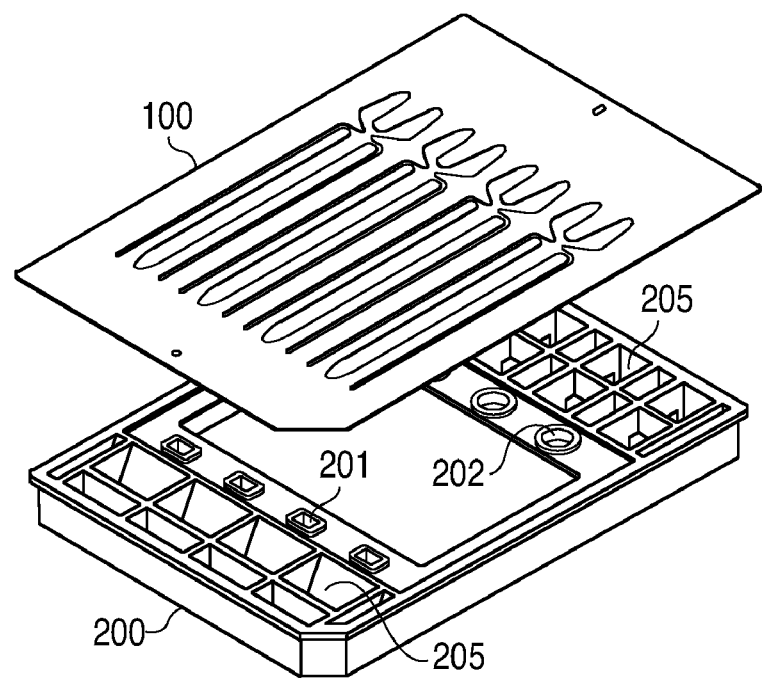
FIGS. 2A and 2B are schematic illustrations of the multilayer fluidic card of FIG. 1 positioned adjacent to a caddy containing reservoirs, in accordance with the present invention, FIG. 2A showing the card uppermost and FIG. 2B showing the caddy uppermost.

Bottom sheet 130 provides a closed bottom surface for channels 122 in channel sheet 120, resulting in the channels being disposed within the card. Alternatively, channel sheet 120 and top sheet 110 may be combined in a single shaped layer that includes channels 122 etched, molded, or otherwise formed into the single layer, as seen, for example, in FIGS. 6A and 6B and described below. In this alternative, the shaped layer will also include electrodes, vias, and wells. In yet another alternative, channel sheet 120 and bottom sheet 130 may be combined in a single shaped layer that includes channels 122 etched, molded, or otherwise formed into the single layer. When viewed from the top, such a structure would appear similar to structure 100 as it is shown in FIG. 2A. In still another alternative, not shown, the card structures may be formed into the caddy, so that the card consists of only a bottom sheet.

FIG. 1B shows multilayer card 100 assembled, with top sheet 110 aligned with channel sheet 120, which is aligned with bottom sheet 130. The three sheets are bonded together using methods known in the art. Channels 122 are shown in FIG. 1B as if seen through a translucent or transparent top sheet 110. However, if optical detection is required, top sheet 110 may be opaque to prevent unwanted excitation and fluorescence of the liquid contained in the channels, and bottom sheet 130 may be transparent to permit detection. Various detection schemes may be employed with devices according to the present invention, and so the layers may be formed from whatever material is appropriate to either prevent excitation or permit detection. The same material or different materials may be employed in the various layers, with poly(methyl methacrylate) (PMMA) and cyclic olefin copolymer (COC) being just two possible materials.

Figure 2B:
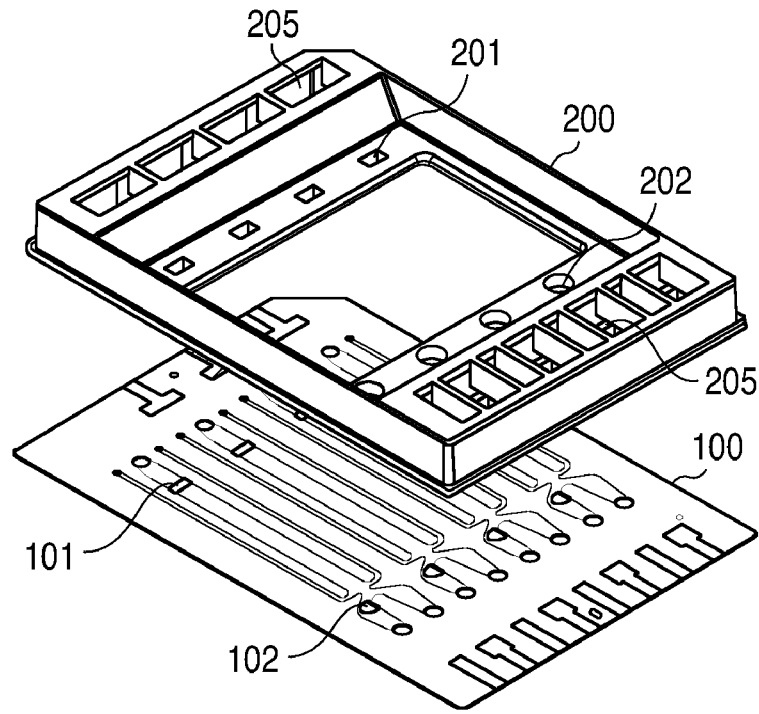

FIGS. 2A and 2B show exploded views of multilayer card 100 and a caddy 200, with the card uppermost in FIG. 2A and the caddy uppermost in FIG. 2B. In operation, the caddy would be uppermost as shown in FIG. 2A. The configuration of reservoirs 205 in caddy 200 is determined by the configuration of vias 114 in top sheet 110, which, as described above, is based on the configuration of the channel or channels 122 in channel sheet 120. Thus, while one configuration of reservoirs, vias, and channels is illustrated in the figures, embodiments of the device admit variation in the number and configuration of the various structures to help improve operational efficiency. When used to carry out an electrophoretic separation, a card includes a minimum of one channel, two vias, and two electrodes, while the caddy includes a minimum of two reservoirs.

Caddy 200 is bonded to card 100 as seen in FIG. 3A, resulting in a device having electrically isolated electrodes feeding into separated channels. Because card 100 is slightly larger than caddy 200, a portion of each electrode extends beyond the caddy and is accessible at the edge of the card as seen in FIG. 3A. As is evident from FIGS. 2A and 2B, when caddy 200 is mated with card 100, each reservoir 205 overlaps both a portion of an electrode 112 and a via 114. When a liquid is introduced into the reservoir, the liquid provides a conductive path between the electrode and a channel in fluid communication with the via. Thus, dry electrical contact can be made at the edge of the device that transfers current through the electrodes into the liquid-containing reservoirs. Therefore, an electrical contact that is included in an instrument designed to operate the device can be configured to contact only the portion of an electrode that extends beyond caddy 200 and not any liquid contained within the device, thereby avoiding cross-contamination between devices that are inserted into the instrument. As is evident from FIGS. 1A and 1B, wells 101 and 102 in the card are in fluid communication with channels 122. Wells 201 and 202 in caddy 200 are aligned with wells 101 and 102 in the card as seen in FIG. 2B, thereby permitting one or more samples to be introduced into the device through wells 201 and 101 and one or more isolated sample components to be removed from the device through wells 202 and 102.

While it is presently preferred that the card be slightly larger than the caddy as described above, allowing a portion of each electrode to extend beyond the caddy, in alternative embodiments, the caddy and the card could be the same size or the caddy could even be larger than the card. In these alternatives, the portions of the electrodes disposed outside the reservoirs could be accessible through openings formed in the caddy or indentations in the edges of the caddy.

FIGS. 3B and 3D show additional structures 215 that can be included in the reservoirs 205 of caddy 200. These structures can prevent a separation matrix contained within a channel from flowing onto an electrode while allowing electrical contact by means of a buffer that touches both the separation matrix and the electrode.

Another embodiment of a fluidic device having incorporated electrodes, in accordance with the present invention, is illustrated in FIGS. 4A-8B. The illustrated device comprises a multilayer fluidic card 400 and a caddy 500. In this embodiment, the electrodes are incorporated into the caddy rather than into the fluidic card. The multilayer card comprises a channel sheet 420 and a bottom sheet 430. Channel sheet 420 includes wells 401 and 402, vias 414, and channels 422. Electrodes 512 are disposed on deformable tabs 516 located on the top surface of caddy 500. Caddy 500 also includes wells 501 and 502 and reservoirs 505.

In the present embodiment, multilayer card 400 includes two layers: a shaped layer and a flat layer. The shaped layer, channel sheet 420, is best seen in FIGS. 6A and 6B. FIG. 4A shows the top surface of channel sheet 420. The bottom surface of channel sheet 420 would appear similar to the view seen in FIG. 5B. In FIG. 5B, which shows the bottom surface of the fluidic device, channels 422 are shown as if seen through a translucent or transparent bottom sheet 430. Vias 414 pass entirely through channel sheet 420 and can be seen in all of FIGS. 4A, 5B, 6A, and 6B. Vias 414 may be formed using any appropriate technique known in the art, for example molding, etching, drilling, and laser cutting. In the present embodiment, channels 422 are machined into the bottom surface of sheet 420, but they may be formed using other techniques, e.g., molding, etching, stamping, and grinding. As is best seen in FIG. 6A, vias 414 provide fluid communication with channels 422. Bottom sheet 430 provides a closed bottom surface for channels 422 in channel sheet 420.

Alternative embodiments of multilayer card 400 are, of course, possible. For example, the multilayer card may include a top sheet, channel sheet, and bottom sheet, with vias and wells formed in the top sheet and channels formed in the channel sheet in the appropriate configurations, and the bottom sheet providing a closed bottom surface for the channels. Such a structure would appear similar to the multilayer fluidic card seen in FIG. 1A but without electrodes disposed on the surface of the card. In still another alternative, the card structures may be formed into the caddy, so that the card consists of only a bottom sheet.

Various detection schemes may be employed with devices according to the present embodiment, and so the layers of the multilayer fluidic card may be formed from whatever material is appropriate to either prevent excitation or permit detection. The same material or different materials may be employed in the various layers, with PMMA and COC being just two possible materials.

Caddy 500 includes both electrodes 512 and reservoirs 505. Electrodes 512 are disposed on deformable tabs 516 to form electrode/tab structures on the top surface of caddy 500. In the present embodiment, electrodes 512 are fabricated using a carbon conductive paste. In alternative embodiments, the electrodes may comprise different or additional materials, including, for example, gold, copper, platinum, silver/silver chloride paste, and other conductive materials. The electrodes may be patterned onto deformable tabs 516 by screen printing, pad printing, ink-jet printing, stenciling, or other similar methods. In addition, the electrodes may be formed on the tabs using a co-injection molding or an over-molding process. In alternative embodiments, electrodes 512 may be metal (or another conductive material) pieces bonded to caddy 500 or insert molded into the caddy. In these embodiments, electrodes 512 and deformable tabs 516 are integral structures rather than the electrodes being formed separately onto the deformable tabs.

The electrodes may comprise a single material or may comprise multiple materials. As in the previously described embodiment, multiple materials may be used where an electrode material has high conductivity but is incompatible with liquids to be used in and with the device. In this case, electrodes may be fabricated by applying a chemically compatible material (e.g., a carbon conductive paste) to regions of deformable tabs 516 that will come into contact with a liquid, applying a second material (e.g., a high-conductivity material such as silver) outside of the regions of the tabs that contact a liquid, and connecting the second material to the chemically compatible material. Alternatively, a chemically incompatible conductive material may be applied first to deformable tabs 516 and then covered completely with a chemically compatible conductive material. As a result, low electrical resistance is achieved, but any liquid within the device is exposed only to a chemically compatible material.

Figure 7A:
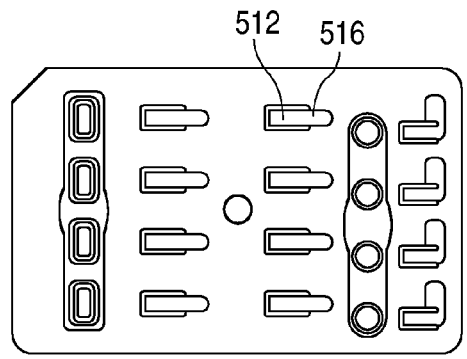
Figure 7B:
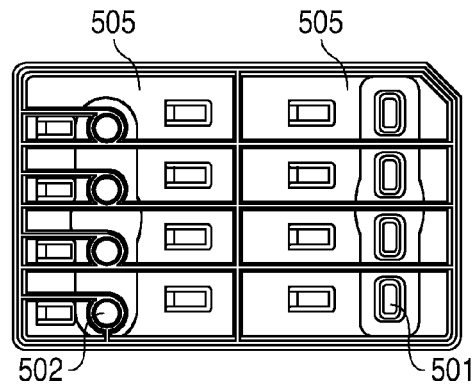

The deformable tabs are fabricated in a first position in the plane of the upper surface of the caddy. The tabs are deformed out of plane into a second position during a later stage of manufacture of the device. Thus, the term "deformable tab" is defined herein as a tab that is fabricated in a first (not deformed) position and that assumes a second (deformed) position during a later stage of manufacture of the device. In the second position, at least a portion of each tab 516 extends downward into one of reservoirs 505. FIGS. 7A and 7D, for example, shows deformable tabs 516 in the first position, while FIG. 5C shows the tabs in the second position. Electrodes 512 may be formed on (or bonded to or molded into) the deformable tabs either before or after the tabs are deformed into the second position.

It may be advantageous to minimize the stress in the tab/electrode structure because the resistance of the electrode may increase when stretched or the electrode and/or tab may fracture when deformed. In one embodiment, it may be preferred to deform the tab/electrode structure in the shape of an arc, rather than at an angle as shown in FIG. 5C, where the deformation of the tab/electrode structure is localized at a hinge point. Alternatively, or in addition, the tab/electrode structure could have multiple deformation points instead of a single one as shown in FIG. 5C. The deformation point(s) may also be thinned to reduce stress. One means for thinning can be seen as semi-circular cutouts at 517 in FIG. 5C.

Caddy 500 is bonded to card 400 as seen in FIG. 4B and FIGS. 5A-5C. Either before or after the caddy and card are bonded together, each electrode/tab structure is deformed out of plane, as shown in FIG. 5C. The electrode/tab structures are sized such that when reservoirs 505 contain a liquid, the electrodes reach down into the liquid. In this way, dry electrical contact can be made on the top of caddy 500 to transfer current into the liquid. Features (not shown) could be included on the top of the card or as part of the caddy that lock the electrode tabs in place after deforming.

While the figures show the contact areas for the dry electrodes spread out across the top of the device, the conductive traces could be routed to a single, more confined region of the device. This type of arrangement is often preferred for supporting a common electrical interface.

The configuration of reservoirs 505 in caddy 500 is partially determined by the configuration of vias 414 in channel sheet 420, as when a liquid is introduced into a reservoir, the liquid provides a conductive path between the electrode 512 that reaches down into the liquid and a channel 422 through a via 414. One configuration of reservoirs, vias, and channels is illustrated in the figures; however, embodiments of the device admit variation in the configuration of the various structures to help improve operational efficiency.

Figure 7C:
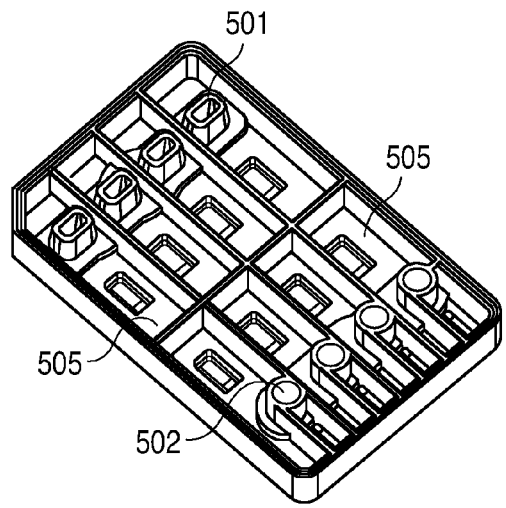
Figure 7D:
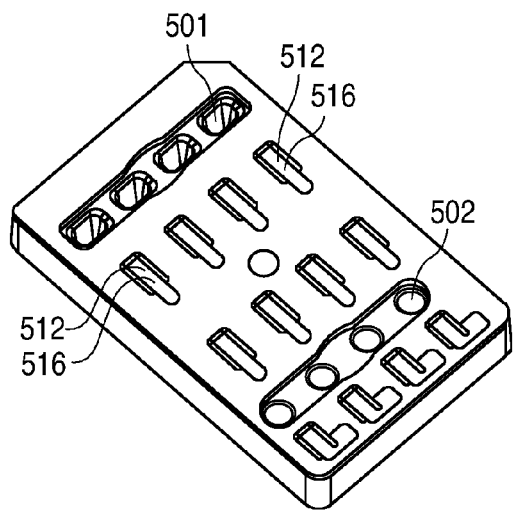

One particular advantage to the reservoir configuration of the present embodiment, which is best seen in FIG. 5C and FIG. 7C, is that when caddy 500 is joined to card 400, reservoirs 505 are directly above channels 422, in which electrophoresis may be carried out. In this configuration, liquid in the reservoirs positioned directly over the channels acts as a heat sink that can absorb joule heating during the electrophoresis process. In addition, this configuration is very compact and allows for a minimal total volume for the device. Reservoirs 505 are sized such that in combination they extend over an area covering substantially all of each of the channels of the device. This can be seen, for example, in FIG. 5C. It will be appreciated that all of reservoirs 505 may be of equal size or may, alternatively, be of unequal size.

A patterned/punched label, seen at 600 in FIGS. 4A, 8A, and 8B, may be added on top of the caddy so that liquid within the device is completely sealed from the outside environment but openings are provided in the label to allow contact to the dry electrodes. As seen in FIG. 8A, label 600 may comprise two layers, a cover sheet 610 and a patterned/punched sheet 620. Cover sheet 610 is removed by the user of the device, leaving patterned/punched sheet 620 in place over caddy 500.

Where a label is included in the device, the electrodes may be printed onto (or otherwise disposed on) the label rather than on the caddy. For example, electrode tabs could be incorporated into a flexible label as punch outs. In another embodiment, a laminate that includes molded plastic fingers could be applied on top of the caddy instead of being molded as part of the caddy. In either of these embodiments, the caddy itself would not be fabricated with deformable tabs, just openings above the reservoirs. Prior to use, the electrode tabs on the label would be punched and pushed into the reservoirs, or the molded plastic fingers would be bent so as to make electrical contact with a liquid in the caddy reservoirs. These alternative embodiments would not appear substantially different from the embodiment illustrated in the figures.

The device could also include blister packs for reagent storage. This would be desirable if some reagents are not stable when stored mixed in the device or otherwise need to be kept separate until point of use. The blister pack could be burst by the user or the instrument, releasing the stored reagent(s) into the reservoirs at the appropriate time.

Plugs (or combs) 701 and 702 can be seen in the figures. These are included to help ensure that wells 501 and 502 in caddy 500 and wells 401 and 402 in card 400 remain free of any separation matrix contained within the device during manufacturing, shipping, and storage. The plugs are removed prior to using the device, permitting one or more samples to be introduced into the device and one or more isolated sample components to be removed from the device through wells 501 and 502, respectively, in the caddy, wells 501 and 502 being aligned with wells 401 and 402 in the card.

Yet another embodiment of a fluidic device having incorporated electrodes, in accordance with the present invention, is illustrated in FIGS. 9A-10D. The illustrated device comprises a multilayer fluidic card and a caddy 900. In this embodiment, as in the previous embodiment, the electrodes are incorporated into the caddy rather than into the fluidic card. As illustrated in FIG. 9A, the multilayer card is card 400, which is also illustrated in FIG. 4A and has been described above. Alternative multilayer cards have also been described above and may be used in place of the illustrated card 400. A separation matrix 924 is disposed within at least a portion of one or more of the channels included in the multilayer card. Caddy 900 includes wells 901 and 902, reservoirs 905, and electrodes 912. The device further includes a seal 915, vents 918, and a barcode label 925.

In the present embodiment, electrodes 912 are independent structures (i.e., structures that are fabricated separately from the caddy) that are incorporated into caddy 900 by being inserted (e.g., by being driven or press-fit) into the caddy. As seen in FIG. 9A, openings 903 are provided in the caddy through which electrodes 912 extend. Electrodes 912 are shown in place within openings 903 in FIG. 10D. While electrodes 912 are illustrated in the figures as straight metal pins, they may take shapes other than the one illustrated and may be fabricated from and/or coated with a conductive material other than a metal.

Electrodes 912 may be integrated into caddy 900 either before or after the caddy is bonded to card 400. An upper portion of each electrode remains accessible on the upper surface of the device while a lower portion extends down into the reservoir over which the electrode is positioned. The electrodes are sized such that when reservoirs 905 contain a liquid, the electrodes extend down into the liquid. Thus, dry electrical contact can be made on the top of caddy 900 to transfer current into the liquid contained within reservoirs 905.

The configuration of reservoirs 905 in caddy 900 is partially determined by the configuration of the vias in the fluidic card. While one configuration of reservoirs, vias, and channels is illustrated in the figures, embodiments of the device admit variation in the configuration of the various structures to help improve operational efficiency. However, as noted above, one particular advantage to the reservoir configuration of both the present and the previous embodiment is that the reservoirs are directly above the channels. Where the channels are used for electrophoresis, liquid in the reservoirs positioned directly over the channels acts as a heat sink to absorb joule heating during the electrophoresis process. Reservoirs 905 are sized such that in combination they extend over an area covering substantially all of each of the channels of the device. This can be seen, for example, in FIG. 10D. It will be appreciated that all of reservoirs 905 may be of equal size or may, alternatively, be of unequal size.

Seal 915 may be a solid sheet of material, such as a heat-seal polymer or foil, that is used to cover the device during shipping. Alternatively, a patterned/punched label such as is seen at 600 in FIGS. 4A, 8A, and 8B may be used. Note that various raised areas are provided on the surface of caddy 900. These are especially important when seal 915 comprises a heat seal and are used to concentrate heat and pressure near regions that must be sealed (e.g., wells) and to protect other regions from contact with the seal (e.g., the exposed upper surfaces of the electrodes). The features have narrow rims to reduce the force that a user must exert to peel off the seal before using the device. These features may be eliminated if a seal is not used with the device.

Vents 918 are included to protect a sealed device from damage during shipping and storage. If a device is subjected to conditions such as, for example, heat or reduced pressure while seal 915 is in place, the portion of seal 915 affixed over the area of a plug 701 or 702 may expand, creating a vacuum within the plug area. If the vacuum is not otherwise relieved, it can extend beneath the plug and through one or more of caddy wells 901 or 902 into the associated well(s) 401 and 402 within the fluidic card. As can be best seen in FIGS. 9A and 10D, each of wells 401 and 402 within the fluidic card is fluidly connected with a channel 422. A vacuum that acts on any of these wells can draw a separation matrix 924 disposed within the channel 422 out of the channel and into the well, affecting the utility of the device. To eliminate the possibility of a vacuum being communicated from a plug area to a channel through one or more wells, vents 918 are positioned adjacent to the wells as seen, for example, in FIGS. 9A, 10A, and 10C. Referring now to FIG. 10C, it can be seen that vents 918 connect each plug area with a reservoir 905 below. By connecting the plug area to the reservoir, which is only partially filled with a fluid (e.g., a buffer), any vacuum created during shipping or storage is transferred to the air space over the fluid within the reservoir. Because the volume of the reservoir is much larger than the extra volume created by the expansion of the portion of the seal affixed over the plug area, the vacuum created by the seal expansion is damped out (by the ratio of the volumes). Additionally, each vent 918 creates a pressure short circuit between a well and a via as can be seen, for example, between well 401 and via 414 in FIG. 10D. Therefore, even if there is some residual pressure change due to expansion of the seal, there is no pressure difference between the channel and the well, and the separation matrix does not flow out of the channel.

In the present embodiment, label 925 includes a 2D barcode. The barcode may encode, for example, lot- or batch-specific information for the device.

It should be noted that a caddy similar to those seen in FIGS. 5C, 7C, 10C, and 10D (i.e., a caddy having reservoirs that extend over the area occupied by channels and/or chambers in a fluidic device, thereby acting as a heat sink for the channels and/or chambers) will offer advantages in any number of fluidic devices, not only fluidic devices incorporating electrodes, but also fluidic devices that are operated using electrodes located separate from the device in a system designed to receive the fluidic device.

Thus, another aspect of the present invention is a fluidic device configured to absorb joule heating within the device, the device comprising a card and a caddy. Such a device would be, in effect, a device such as those that have been described above but without the electrodes. The card may be any of the cards described above and illustrated in the figures. The card comprises a channel having first and second ends, the channel disposed within the card. The card further comprises first and second vias in fluid communication with the channel through an upper surface of the card. The first via is positioned adjacent to the first end of the channel, and the second via is positioned adjacent to the second end of the channel. The caddy comprises at least first and second reservoirs and may appear similar to the caddy seen in FIG. 7C. The caddy is attached to the card such that the first reservoir is positioned over the first via and the second reservoir is positioned over the second via. The first and second reservoirs are sized such that the two reservoirs in combination extend over an area covering substantially all of the channel disposed within the card.

Another aspect of the present invention is a system for isolating one or more sample components of a sample material following separation of the sample material into a plurality of sample components. The system comprises a device such as those that have been described above as well as instrumentation for controlling the device. For example, the instrumentation may comprise a detector positioned in sensory communication with a detection region of the device, a processor operably coupled to the detector and to a fluid direction system that is configured to control movement of one or more sample components based on information received from the detector. As used herein, the phrase "in sensory communication" refers to positioning of a detector such that it is operably connected to the device, i.e., capable of receiving a detectable signal from the contents of the device. In the case of optical signals, this requires only that the detector be positioned to receive the optical signal. The system may be configured to simultaneously control multiple channels or multiple fluidic circuits. In such a configuration, the fluid direction system may be configured to control the movement of one or more sample components in one channel or fluidic circuit based on information received by the detector in a parallel channel or circuit. Fluid movement may be controlled by the use of electrokinetics, such as electrophoresis or electroosmosis, wherein charged components within the fluid move, and/or the fluid itself moves, in response to the application of positive and negative voltages. Another example includes the application of positive or negative partial pressure to certain areas of the device, so that fluid moves from locations of high pressure to locations of low pressure through the channel or channels of the device. Partial pressures may be applied by a pumping mechanism or the application of a vacuum force to a reservoir. Therefore, the fluid direction system includes the capabilities for providing and controlling forces to move fluids or fluid components through the channel or channels of the device.

Yet another aspect of the present invention is a method for manufacturing a fluidic device having incorporated electrodes. In a first method, a card and a caddy are provided. The card comprises a channel, first and second vias, and first and second electrodes. The channel is disposed within the card and has first and second ends. The first and second vias are in fluid communication with the channel through an upper surface of the card. The first and second electrodes are disposed on the upper surface of the card. The first via and first electrode are positioned adjacent to the first end of the channel, and the second via and second electrode are positioned adjacent to the second end of the channel.

The caddy includes first and second reservoirs. The caddy is attached to the card such that the first reservoir is positioned over the first via and a portion of the first electrode, the second reservoir is positioned over the second via and a portion of the second electrode, and a portion of each of the first electrode and the second electrode is accessible for dry electrical contact.

In a second method for manufacturing fluidic devices having incorporated electrodes, a card and a caddy are provided. The card comprises a channel and first and second vias. The channel is disposed within the card and has first and second ends. The first via is in fluid communication with the channel through an upper surface of the card and is positioned adjacent to the first end of the channel. The second via is in fluid communication with the channel through the upper surface of the card and is positioned adjacent to the second end of the channel.

The caddy comprises first and second reservoirs and first and second electrodes. The first electrode is positioned over the first reservoir, and the second electrode is positioned over the second reservoir. In one embodiment of the caddy, the first electrode is disposed on a first deformable tab, and the second electrode is disposed on a second deformable tab. The tabs are formed on the caddy in a first position and are then deformed out of plane into a second position. The electrodes may be formed on the tabs either before or after the tabs are deformed, and the tabs may be deformed either before or after the caddy is attached to the card. In a second embodiment of the caddy, the first and second electrodes are independent structures (e.g., metal pins) that are incorporated into the caddy by being inserted (driven or press-fit) into openings provided in the caddy. In this embodiment, the electrodes may be incorporated into the caddy either before or after the caddy is attached to the card.

The caddy is attached to the card such that the first reservoir is positioned over the first via and the second reservoir is positioned over the second via and such that a portion of each of the first electrode and the second electrode is accessible for dry electrical contact.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A fluidic device having incorporated electrodes, comprising:
    a card comprising
        a channel disposed within the card, the channel having first and second ends;
        first and second vias in fluid communication with the channel through an upper surface of the card; and
        first and second electrodes disposed on the upper surface of the card;
        wherein the first via and first electrode are positioned adjacent to the first end of the channel and the second via and second electrode are positioned adjacent to the second end of the channel;
    a caddy comprising
        first and second reservoirs;
    wherein the caddy is attached to the card such that
        the first reservoir is positioned over the first via and a portion of the first electrode,
        the second reservoir is positioned over the second via and a portion of the second electrode, and
        a portion of each of the first electrode and the second electrode is accessible for dry electrical contact.

2. The device of claim 1 wherein the card is larger than the caddy such that a portion of each electrode extends beyond the caddy and is accessible at an edge of the card.

3. The device of claim 1 wherein the card comprises a top sheet, a channel sheet, and a bottom sheet, and wherein the vias extend through the top sheet, the electrodes are disposed on an upper surface of the top sheet, the channel is formed in the channel sheet, and the bottom sheet provides a closed bottom surface for the channel.

4. The device of claim 3 wherein the top sheet and the channel sheet are combined in a single shaped layer.

5. The device of claim 3 wherein the channel sheet and the bottom sheet are combined in a single shaped layer.

6. The device of claim 1 further comprising a liquid disposed in each of the first and second reservoirs, wherein the liquid disposed in the first reservoir provides a conductive path between the first electrode and the first end of the channel through the first via, and wherein the liquid disposed in the second reservoir provides a conductive path between the second electrode and the second end of the channel through the second via.

7. The device of claim 1 wherein the caddy further comprises a structure that prevents a separation matrix contained within the channel from flowing onto one or both of the first and second electrodes.

8. The device of claim 1 wherein the card further comprises first and second wells in fluid communication with the channel, and wherein the caddy further comprises first and second wells aligned with and in fluid communication with the first and second wells in the card.

9. A fluidic device having incorporated electrodes, comprising:
    a card comprising
        a channel disposed within the card, the channel having first and second ends; and
        first and second vias in fluid communication with the channel through an upper surface of the card, the first via positioned adjacent to the first end of the channel, and the second via positioned adjacent to the second end of the channel;
    a caddy comprising
        first and second reservoirs; and
        first and second electrodes, wherein the first electrode is positioned such that a first portion of the first electrode extends into the first reservoir and a second portion of the first electrode is accessible for dry electrical contact, and wherein the second electrode is positioned such that a first portion of the second electrode extends into the second reservoir and a second portion of the second electrode is accessible for dry electrical contact;
    wherein the caddy is attached to the card such that the first reservoir is positioned over the first via and the second reservoir is positioned over the second via.

10. The device of claim 9 wherein the card comprises a top sheet, a channel sheet, and a bottom sheet, and wherein the vias extend through the top sheet, the channel is formed in the channel sheet, and the bottom sheet provides a closed bottom surface for the channel.

11. The device of claim 10 wherein the top sheet and the channel sheet are combined in a single shaped layer.

12. The device of claim 10 wherein the channel sheet and the bottom sheet are combined in a single shaped layer.

13. The device of claim 9 further comprising a liquid disposed in each of the first and second reservoirs, wherein the liquid disposed in the first reservoir provides a conductive path between the first electrode and the first end of the channel through the first via, and wherein the liquid disposed in the second reservoir provides a conductive path between the second electrode and the second end of the channel through the second via.

14. The device of claim 9 wherein the card further comprises first and second wells in fluid communication with the channel, and wherein the caddy further comprises first and second wells aligned with the first and second wells in the card.

15. The device of claim 9 wherein the first and second reservoirs are sized such that the reservoirs in combination extend over an area covering substantially all of the channel.

16. The device of claim 9 wherein the card comprises a plurality of channels.

17. The device of claim 16 wherein the first and second reservoirs are sized such that the reservoirs in combination extend over an area covering substantially all of each of the plurality of channels.

18. The device of claim 16 wherein each channel has a first end and a second end and wherein a via is positioned adjacent to each first end of each channel and each second end of each channel.

19. The device of claim 18 wherein the first reservoir extends over all of the vias positioned over first ends of the channels and the second reservoir extends over all of the vias positioned over second ends of the channels.

20. The device of claim 9 wherein the caddy further comprises openings provided in the caddy, and wherein the first and second electrodes are fabricated as structures independent of the caddy and are inserted into the openings in the caddy.

21. The device of claim 9 wherein the first electrode is disposed on a first deformable tab and the second electrode is disposed on a second deformable tab.

22. The device of claim 21 wherein the deformable tabs are formed into an upper surface of the caddy.

23. The device of claim 21 wherein the deformable tabs are attached to an upper surface of the caddy.

24. The device of claim 21 further comprising a label attached to an upper surface of the caddy.

25. The device of claim 24 wherein the deformable tabs are formed into the label.

26. The device of claim 24 wherein the deformable tabs are attached to the label.

27. The device of claim 21 wherein the deformable tabs are deformed during manufacture such that a portion of the first electrode extends downward into the first reservoir and a portion of the second electrode extends downward into the second reservoir.

28. The device of claim 21 wherein the deformable tabs are configured to deform one or both of at a hinge point and in the shape of an arc.

29. The device of claim 21 wherein each deformable tab includes one or more thinned areas to reduce stress when the tab is deformed.

30. The device of claim 13 wherein the first electrode is disposed on a first deformable tab and the second electrode is disposed on a second deformable tab, and wherein the deformable tabs are deformed such that a portion of the first electrode is disposed within the liquid disposed in the first reservoir and a portion of the second electrode is disposed within the liquid disposed in the second reservoir.

31. The fluidic device of claim 9, the device further comprising:
    first and second wells disposed in the caddy such that they are in fluid communication with the channel disposed within the card; and
    first and second vents disposed in the caddy adjacent to the first and second wells, the first vent in fluid communication with the first reservoir and the second vent in fluid communication with the second reservoir, wherein the vents equilibrate pressure differences that result when a seal that is affixed over the first and second wells expands, creating a vacuum beneath the seal.

32. A fluidic device configured to absorb joule heating within the device, comprising:
    a card comprising
        a channel disposed within the card, the channel having first and second ends; and
        first and second vias in fluid communication with the channel through an upper surface of the card, the first via positioned adjacent to the first end of the channel, and the second via positioned adjacent to the second end of the channel;
    a caddy comprising
        first and second reservoirs
    wherein the caddy is attached to the card such that the first reservoir is positioned over the first via and the second reservoir is positioned over the second via, and wherein the first and second reservoirs are sized such that the two reservoirs in combination extend over an area covering substantially all of the channel.

33. A system for isolating one or more sample components of a sample material following separation of the sample material into a plurality of sample components, comprising:
    a fluidic device having incorporated electrodes comprising a card and a caddy, the card comprising a channel disposed within the card, the channel having first and second ends; a first via in fluid communication with the channel through an upper surface of the card, the first via positioned adjacent to the first end of the channel; and a second via in fluid communication with the channel through the upper surface of the card, the second via positioned adjacent to the second end of the channel; the caddy comprising first and second reservoirs and first and second electrodes, the first electrode positioned such that a first portion of the first electrode extends into the first reservoir and a second portion of the first electrode is accessible for dry electrical contact, the second electrode positioned such that a first portion of the second electrode extends into the second reservoir and a second portion of the second electrode is accessible for dry electrical contact; wherein the caddy is attached to the card such that the first reservoir is positioned over the first via and the second reservoir is positioned over the second via, and wherein a portion of each of the first electrode and the second electrode is accessible for dry electrical contact;
    a detector in sensory communication with the device;
    a fluid direction system; and
    a processor operably coupled to the detector and the fluid direction system.

34. A method of manufacturing a fluidic device having incorporated electrodes, the method comprising:
    providing a card comprising a channel disposed within the card, the channel having first and second ends; a first via in fluid communication with the channel through an upper surface of the card, the first via positioned adjacent to the first end of the channel; and a second via in fluid communication with the channel through the upper surface of the card, the second via positioned adjacent to the second end of the channel;
    providing a caddy comprising first and second reservoirs and first and second electrodes, wherein the first electrode positioned such that a first portion of the first electrode extends into the first reservoir and a second portion of the first electrode is accessible for dry electrical contact, the second electrode positioned such that a first portion of the second electrode extends into the second reservoir and a second portion of the second electrode is accessible for dry electrical contact; and attaching the caddy to the card such that the first reservoir is positioned over the first via and the second reservoir is positioned over the second via.

35. The method of claim 34 wherein the first electrode is disposed on a first deformable tab and the second electrode is disposed on a second deformable tab, the method further comprising deforming the deformable tabs such that a portion of the first electrode extends downward into the first reservoir and a portion of the second electrode extends downward into the second reservoir.

36. The method of claim 34 wherein the first and second electrodes are fabricated as structures independent of the caddy, the method further comprising inserting the first and second electrodes into openings in the caddy.

* * * * *